Sept. 21, 1954 R. V. LINDQUIST Plant Pat. 1,304
ROSE PLANT
Filed Dec. 4, 1952 2 Sheets-Sheet 1
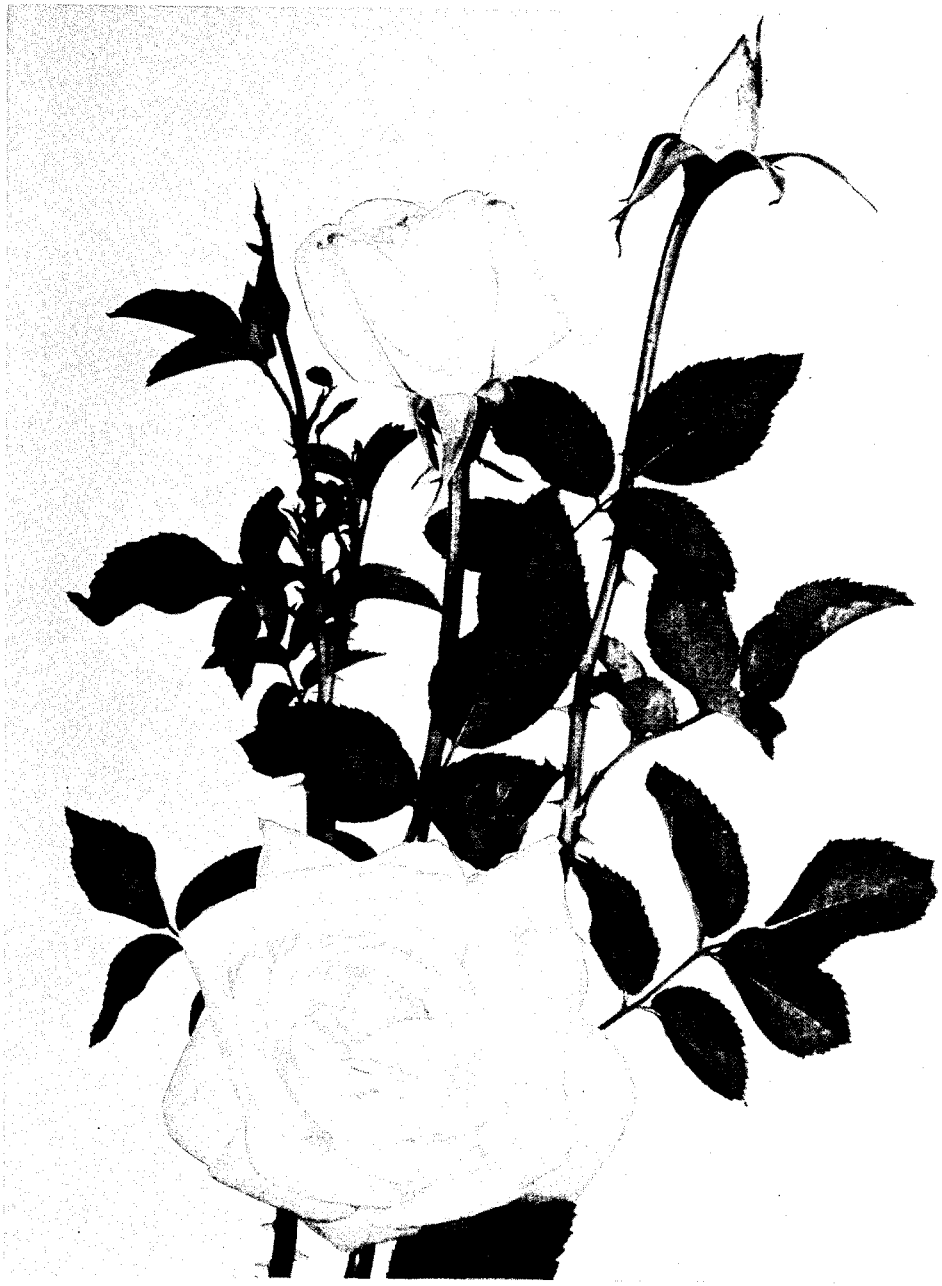
Inventor.
R. V. Lindquist
By: Robbins Cobb
Attorneys.

Sept. 21, 1954 R. V. LINDQUIST Plant Pat. 1,304
ROSE PLANT
Filed Dec. 4, 1952 2 Sheets-Sheet 2
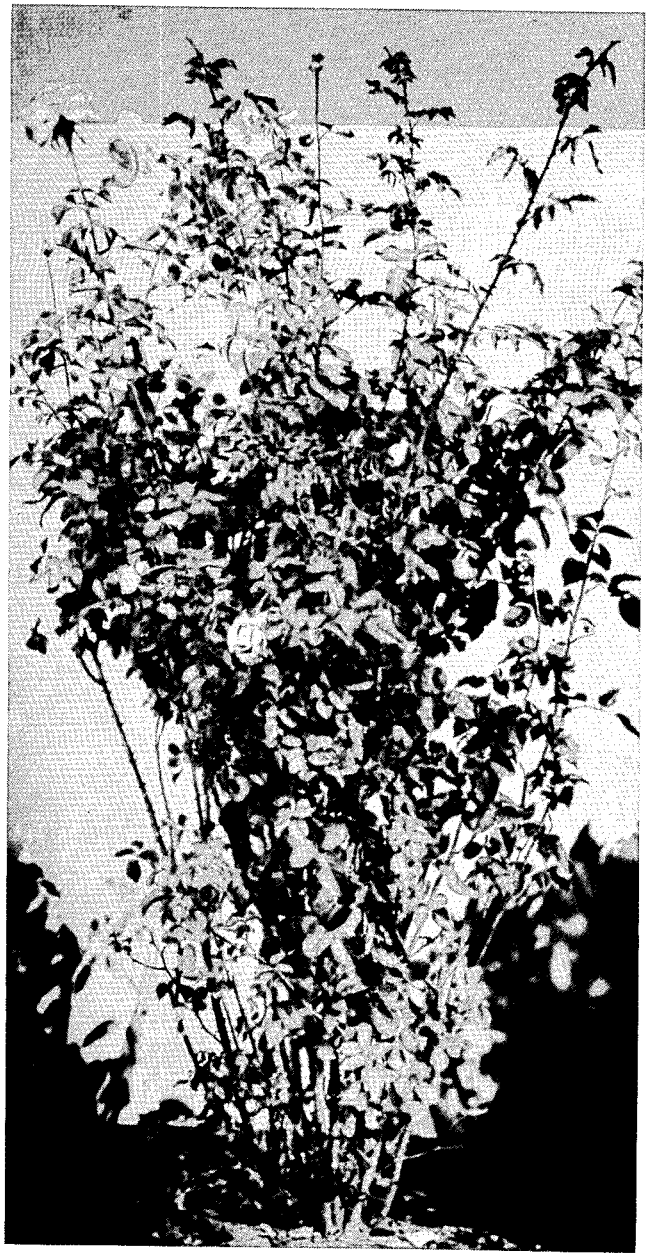
Inventor
R. V. Lindquist
By: Robb & Robb
Attorneys.

Patented Sept. 21, 1954

Plant Pat. 1,304

UNITED STATES PATENT OFFICE 1,304

ROSE PLANT

Robert V. Lindquist, Hemet, Calif., assignor to Hemet Wholesale, Hemet, Calif., a partnership Application December 4, 1952, Serial No. 324,155

1 Claim. (Cl. 47—61)

The present invention relates to a new and distinct variety of rose plant of the hybrid tea class, which was originated by me by crossing the variety "Charlotte Armstrong" (Plant Patent No. 455) with the variety "Girona" (unpatented).

As the result of this breeding, I have produced a new variety of rose that is particularly characterized as to novelty by its vigorous habit of upright growth; by the distinctive form and color of its buds and flowers in all stages of development; by its habit of bearing flowers singly on exceptionally long, upright, strong and stiff stems; by its distinctively longer and heavier peduncle as compared with other roses of the same class; by the relatively heavy texture of its flower petals, with resultant long-lasting quality of the blooms and their tendency to maintain and preserve their shape until the petals drop; and by the penetrating tea rose fragrance of its flowers.

This combination of characteristics is unique in the class of hybrid tea roses, and definitely distinguishes my new variety from its parents, as well as from all other varieties of which I am aware.

Asexual reproduction of my new variety by budding at Hemet, California, shows that the foregoing characteristics and distinctions come true to form and are established and transmitted through succeeding propagations.

The accompanying drawings show typical specimens of my new variety, one of said drawings depicting the color characteristics of the flowers and foliage in different stages of development, and the other drawing showing a mature plant and depicting its habits of growth, in black-and-white.

The following is a detailed description of my new variety, with color terminology in accordance with Robert F. Wilson's Horticultural Colour Chart (hereinafter abbreviated as "Wilson") and Ridgway's Color Standards and Nomenclature (hereinafter abbreviated as "Ridgway"), as indicated:

Type: Tall; bush; outdoor; seedling; for cut flowers and for garden decoration.

Class: Hybrid tea.

Breeding: Seedling.

*Seed parent.*—"Charlotte Armstrong."

*Pollen parent.*—"Girona."

Propagation: Holds its distinguishing characteristics through succeeding propagations by budding.

*Flower*

Locality where grown and observed: Hemet, California.

Continuity: Continuous during growing season.

Flowers borne: Usually singly to stem; on strong, long stems.

Quantity of bloom: Free, outdoors.

Fragrance: Penetrating; tea.

Bud:

*Peduncle.*—Long; from about 3½ inches to 5 inches in length; average caliper to heavy; erect; stiff; few gland-tipped cilia; numerous prickles. Color—near Lettuce Green, Plate V (Ridgway).

*Before calyx breaks.*—Size—medium. Form—medium length; pointed; ovoid; with a conspicuous neck; with foliaceous appendages; few gland-tipped cilia and glandular bloom on the surface of the bud; usually with foliaceous parts extending beyond the tip of the bud equal to one-fourth or more of its length.

*As calyx breaks.*—Color—near Claret Rose, Plate 021, page 109 (Wilson).

*Sepals.*—Inner surface—with fine, wooly tomentum. Margins—a sepal has either both margins covered or both uncovered, except for the fifth or odd sepal which has wooly tomentum on one margin only; sepals with glandular margins usually have foliaceous appendages; margins without glands have wooly tomentum.

*As first petal opens.*—Size—average to large. Form—medium length to long; pointed to ovoid. Color: outside—base near Dresden Yellow, Plate 64/1, page 64 (Wilson) tipped with near Uranium Green, Plate 63/2, page 63 (Wilson), shading into near Dresden Yellow, Plate 64/2, page 64 (Wilson); central parts of petals near Rose Madder, Plate 23/2, page 23 (Wilson); margin near Rose Madder, Plate 23/1, page 23 (Wilson). Inside—base near Dresden Yellow, Plate 64/1, page 64 (Wilson); becoming near Rose Madder, Plate 23/2, page 23 (Wilson) to near Rose Madder, Plate 23/1, page 23 (Wilson) at margin.

*Opening.*—Opens up well; is not retarded from opening by hot, wet or dry weather.

Bloom:

*Size, when fully open.*—Large; from 4 to 5 inches.

*Petalage.*—Double to very double; from 25 to 30 petals, plus 8 to 14 petaloids; arranged regularly.

*Form.*—High-centered at first; becoming flat to cupped; petals at first being somewhat tightly flat to cupped and rolled outward; becoming later, at maturity, somewhat tightly rolled outward.

Petals:

*Texture.*—Medium thick; moderately leathery, with inside slightly satiny and outside slightly shiny to satiny.

*Shape.*—Outside—round, with apex flat. Intermediate—round, with apex rounded to flat and with one or two notches. Inside—nearly round to obovate; scalloped irregularly; with apex rounded to flat and with one or two notches.

This description of a newly opened flower was made from a rose grown outdoors in the month of September at Hemet, California:

*Color.*—Outside petal: Outside surface—base near Dresden Yellow, Plate 64/2, page 64 (Wilson), shading in center of petal to near Dresden Yellow, Plate 64/1, page 64 (Wilson). Distal parts of petals near Phlox Pink, Plate 625/3, page 77 (Wilson), shading to near Phlox Pink, Plate 625/2, page 77 (Wilson) at margin. Inside surface—base near Dresden Yellow, Plate 64/1, page 64 (Wilson), shading to near Dresden Yellow, Plate 64/2, page 64 (Wilson). Distal parts of petals near Phlox Pink, Plate 625/3, page 77 (Wilson) to near Phlox Pink, Plate 625/2, page 77 (Wilson) at margin. Intermediate petal: Outside surface—base near Dresden Yellow, Plate 64/2, page 64 (Wilson), shading to near Dresden Yellow, Plate 64/3, page 64, (Wilson). Distal parts and margin of petals near Phlox Pink, Plate 625/3, page 77 (Wilson). Inside surface—base near Dresden Yellow, Plate 64/1, page 64 (Wilson), shading to near Dresden Yellow, Plate 64/3, page 64 (Wilson). Center of petals near Phlox Pink, Plate 625/3, page 77 (Wilson), shading towards distal parts of petals to near Phlox Pink, Plate 625/2, page 77 (Wilson); outer margin near Phlox Pink, Plate 625/1, page 77 Wilson). Inner petal: Outside surface—tip of base near Dresden Yellow, Plate 64/1, page 64 (Wilson), shading to near Dresden Yellow, Plate 64/3, page 64 (Wilson). Upper portion of petal near Neyron Rose, Plate 623/2, page 76 (Wilson), shading to near Neyron Rose, Plate 623/1, page 76 (Wilson) at margin. Inside surface—base near Dresden Yellow, Plate 64/1, page 64 (Wilson). Petal becomes near Neyron Rose, Plate 623/1, page 76 (Wilson), shading to near Neyron Rose, Plate 623, page 76 (Wilson) at margin.

This description was made from a rose grown outdoors, and the cut flowers thereof kept for three days indoors at room temperature, in the month of September at Hemet, California:

*Color.*—Outside petal: Outside surface—base near Dresden Yellow, Plate 64/2, page 64 (Wilson), shading to near Dresden Yellow, Plate 64/3, page 64 (Wilson); becoming near Rose Pink, Plate 427/2, page 126 (Wilson). Inside surface—base near Dresden Yellow, Plate 64/2, page 64 (Wilson), becoming near Phlox Pink, Plate 625/3, page 77 (Wilson), shading to near Phlox Pink, Plate 625/2, page 77, (Wilson) toward margin. Inside petal: Outside surface—base near Dresden Yellow, Plate 64/2, page 64 (Wilson), shading to near Dresden Yellow, Plate 64/3, page 64 (Wilson); becoming near Phlox Pink, Plate 625/3, page 77 (Wilson), shading to near Phlox Pink, Plate 625/2, page 77 (Wilson) at margin. Inside surface—base near Dresden Yellow, Plate 64/2, page 64 (Wilson), becoming near Phlox Pink, Plate 625/2, page 77 (Wilson) on balance of petal.

*General color effect.*—Newly opened flower—near Neyron Rose, Plate 623/1, page 76 (Wilson) to near Neyron Rose, Plate 623, page 76 (Wilson); in fully open flower, outer petals become much lighter. Three days open flower—near Phlox Pink, Plate 625/3, page 77 (Wilson).

*Behavior.*—Drop off cleanly except for petaloids; is not particularly affected by cold, hot, wet or dry weather, except as to minor changes in flower color.

*Flower longevity (on bush in garden).*—Three to four days in September.

*Reproductive organs*

Stamens: Many; arranged regularly about pistils; a few mixed with petaloids.

Filaments: Medium length; occasionally has a filament with petaloid attached in place of anther; most with anthers. Color—near Primrose Yellow, Plate 601/1, page 65 (Wilson).

Anthers: Medium size; all open approximately at once. Color: upper side—along margin near Saffron Yellow, Plate 7/1, page 7 (Wilson); under side—near Egyptian Buff, Plate 407, page 122 (Wilson).

Pollen: Moderately abundant. Color—near Saffron Yellow, Plate 7/2, page 7 (Wilson).

Pistils: Many; varying from 100 to 200, but averaging approximately 150 in number.

Styles: Moderately uneven; average length; very thin; somewhat bunched.

Stigma: Color—near Naples Yellow, Plate 403, page 121 (Wilson).

Ovaries: Usually mostly enclosed; some protruding from calyx.

Hips: Average length; turbinate; moderately smooth; walls thick, fleshy. Color—near Courge Green, Plate XVII (Ridgway).

Sepals: Permanent; long; spear-shaped; recurved. Color: inside—near Light Bice Green, Plate XVII (Ridgway), tinted slightly with near Corinthian Purple, Plate XXXVIII (Ridgway), and modified by white tomentum; outside—near Light Bice Green, Plate XVII (Ridgway).

Seeds: Few; usually medium size; from 5 to 12 in number.

*Plant*

Foliage:

*Leaves.*—Compound of usually five to seven leaflets; normal abundance; medium size; moderately heavy; somewhat leathery; semi-glossy.

*Leaflets.*—Shape—oval with apex mucronate. Base—round. Margin—serrate.

*Color.*—Mature: upper surface—near Parsley Green, Plate 00962, page 193 (Wilson); under surface—near Asphodel Green, Plate XLI (Ridgway). Young: upper surface—near Spinach Green, Plate 0960/1, page 187 (Wilson), with some near Corinthian Purple, Plate XXXVIII (Ridgway), becoming more intense toward margin; under surface—near Corinthian Purple, Plate XXXVIII (Ridgway), with some near Spinach Green, Plate 0960/1, page 187 (Wilson) showing through.

*Rachis (the supporting stem of the compound leaf).*—Average size. Upper side—grooved, with some stipitate glands; under side—moderately prickly.

*Stipules.*—Long; medium width; with medium length points turning out at an angle of about 45°.

*Disease.*—Average resistance to mildew, as determined by comparison with other varieties grown under comparable conditions.

Growth:

*Habit.*—Upright; moderately branched.

*Growth.*—Vigorous.

*Canes.*—Medium caliper to heavy.

*Main stems.*—Color—near Chromium Green, Plate XXXII (Ridgway). Large prickles—several to many; medium-length to long; almost straight; moderately broad base. Color—varying from near Cinnamon, Plate XXIX (Ridgway) to near Cinnamon Brown, Plate XV (Ridgway), with some near Hessian Brown, Plate XIII (Ridgway), near base on some thorns. Small prickles—very few. Color—near Cinnamon, Plate XXIX (Ridgway). Hairs—none.

*Branches.*—Color—near Chromium Green, Plate XXXII (Ridgway). Large prickles—several to many; medium-length; almost straight; with moderately narrow base. Color—near Cinnamon Brown, Plate XV (Ridgway). Small prickles — several. Color—near Russet, Plate XV (Ridgway). Hairs—none.

*New shoots.*—Color—near Light Bice Green, Plate XVII (Ridgway). Large prickles—several to many; hooked slightly downward; with medium-length, narrow base. Color — near Biscay Green, Plate XVII (Ridgway), shaded at base with near Deep Hellebore Red, Plate XXXVIII (Ridgway). Small prickles—few. Color—near Biscay Green, Plate XVII (Ridgway), shaded at base with near Deep Hellebore Red, Plate XXXVIII (Ridgway). Hairs—few glandular-tipped hairs.

I claim:

A new and distinct variety of rose plant of the hybrid tea class, substantially as herein shown and described, characterized particularly as to novelty by its vigorous habit of upright growth, by the distinctive form and color of its buds and flowers in all stages of development, by its habit of bearing flowers singly on exceptionally long, upright, strong and stiff stems, by its distinctively longer and heavier peduncle as compared with other roses of the same class, by the relatively heavy texture of its flower petals, with resultant long-lasting quality of the blooms and their tendency to maintain and preserve their shape until the petals drop, and by the penetrating tea rose fragrance of its flowers.

No references cited.